United States Patent [19]

Nocca et al.

[11] Patent Number: 5,364,975
[45] Date of Patent: Nov. 15, 1994

[54] PROCESS FOR THE PRODUCTION OF A TERTIARY ALKYL ETHER COMPRISING A FRACTIONATION SECTION

[75] Inventors: Jean-Luc Nocca; Phillipe Travers, both of Rueil Malmaison; Larry Mank, Orgeval; Alain Forestiere, Vernaison, all of France

[73] Assignee: Institut Francais du Petrole, Rueil-Malmaison, France

[21] Appl. No.: 57,603

[22] Filed: May 5, 1993

[30] Foreign Application Priority Data

Jul. 1, 1992 [FR] France .................. 92 08190

[51] Int. Cl.$^5$ .................................. C07C 41/06
[52] U.S. Cl. ......................................... 568/697
[58] Field of Search ............................. 568/697

[56] References Cited

U.S. PATENT DOCUMENTS

| | | | |
|---|---|---|---|
| 4,503,265 | 3/1985 | Schleppinghoff et al. | 568/697 |
| 4,988,366 | 1/1991 | Harandi et al. | 44/449 |
| 5,237,109 | 8/1993 | Patton et al. | 568/697 |
| 5,258,560 | 11/1993 | Marker | 568/697 |

FOREIGN PATENT DOCUMENTS

| | | |
|---|---|---|
| 0082316 | 6/1983 | European Pat. Off. . |
| 2272063 | 12/1975 | France . |
| 2381010 | 9/1978 | France . |
| 2047706 | 12/1980 | United Kingdom . |
| 92/03401 | 3/1992 | WIPO . |

*Primary Examiner*—Howard T. Mars

[57] ABSTRACT

A process for the preparation of a tertiary alkyl ether, in particular methyl tert. amyl ether (MTAE), is described which comprises reacting, in a reaction section, a charge constituted by a mixture of $C_5$ hydrocarbons, including reactive isopentenes, with an aliphatic monoalcohol in excess, such as methanol, ethanol, propanol or isopropanol, and collecting in the bottom of a fractionation section the corresponding pure tert. alkyl ether. The head effluent, after condensation, is subdivided into a liquid reflux and a distillate. The process is further characterized by providing a finishing reactor for the reflux, or for the reflux + distillate effluent prior to the subdivision thereof, or two finishing reactors are provided, one for the reflux and the other for the distillate, along with the possibility of injecting aliphatic monoalcohol upstream of each finishing reactor.

20 Claims, 2 Drawing Sheets

PROCESS FOR THE PRODUCTION OF A TERTIARY ALKYL ETHER COMPRISING A FRACTIONATION SECTION

SUMMARY OF THE INVENTION

The present invention relates to an improved process for the production of a tertiary alkyl ether by the reaction of at least one isoolefin with an aliphatic monoalcohol in excess. It more particularly relates to the production of tertiary alkyl ethers from at least one isopentene (or isoamylene) and methanol, or other aliphatic monoalcohols such as ethanol, propanol or isopropanol, as well as the production of other tert. alkyl ethers from $C_4$, $C_6$ and $C_7$ isoolefins and said aliphatic monoalcohols (methanol, ethanol, propanol or isopropanol). It more specifically relates to the production of methyl tert. amyl ether (MTAE).

It is known to prepare tertiary alkyl ethers by reacting an isoolefin, generally contained in a hydrocarbon fraction, with an aliphatic alcohol, used generally in excess, in the presence of an acid catalyst, e.g., sulphuric acid, hydrofluoric acid, aluminum chloride or boron fluoride, or in the presence of carbonated materials containing $HSO_3$ groups, e.g., sulphonated charcoals, sulphonated phenol-formaldehyde resins, sulphonated coumarone-indene polymers or, preferably, sulphonated styrenedivinyl benzene copolymer resins.

It has long been known that the reaction between an aliphatic monoalcohol, e.g., with 1 to 3 carbon atoms, and tertiary olefins is balanced and that it is consequently difficult to obtain acceptable isoolefin conversion rates for the recovery of tert. alkyl ethers with a high purity. Therefore, the prior art recommends adding to the main etherification reactor and to the fractionation column for collecting at the bottom the tert. alkyl ether, a finishing reaction section making it possible to increase to a certain extent the production of the sought tert. alkyl ether. The conventional tert. alkyl ether production process will be described hereinafter in conjunction with FIG. 1.

BRIEF DESCRIPTION OF THE DRAWINGS

In FIG. 1, a charge is introduced into a main reaction section represented by the reactor $R_1$. The charge contains a mixture of $C_4$, $C_5$, $C_6$ or $C_7$ hydrocarbons incorporating isoolefins and an aliphatic monoalcohol in excess. The reagents are contacted with an acid catalyst. The product from the reactor $R_1$ is fed into a fractionation section represented by the column $F_1$ in which it is distilled, in order to produce at the bottom a pure tert. alkyl ether and at the head an effluent constituted by non-reactive hydrocarbons contained in the charge, hydrocarbons not converted in the reactor $R_1$, and the excess aliphatic monoalcohol entrained by azeotropy.

Figure 1:
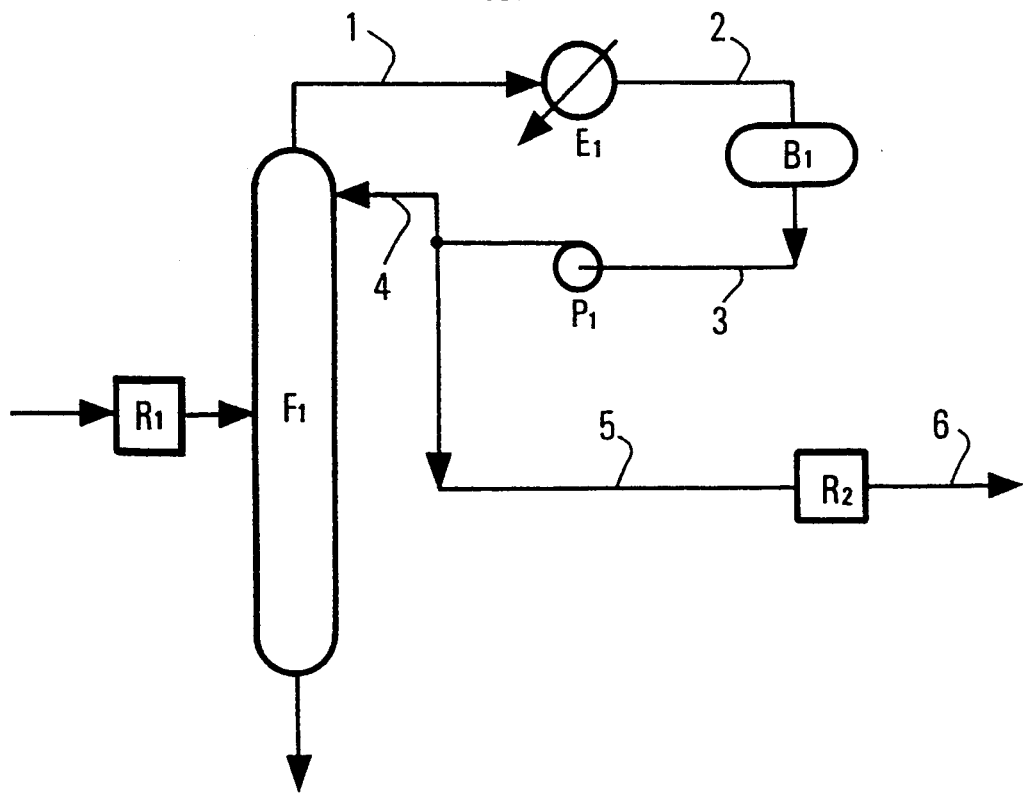
FIG. 1 diagrammatically shows a conventional process for tert. alkyl ether production.

This effluent passing out by the line 1 is condensed in the condenser $E_1$ and collected by the line 2 in the flask $B_1$ from where it is taken up by the line 3 and the pump $P_1$, which passes part of the effluent to the head of the fractionation column $F_1$, as reflux by line 4, and the remainder of the effluent by line 5 to a complementary, finishing reaction section represented by the reactor $R_2$, where the aim is to react in contact with an acid catalyst the largest possible proportion of the hydrocarbons not converted in the main reactor $R_1$ with the excess aliphatic monoalcohol present in the effluent, so as to produce an additional tert. alkyl ether quantity in the effluent passing out of the reactor $R_2$ by the line 6.

However, such a process does not lead to a very high isoolefin conversion and the tert. alkyl ether proportion recovered in the form of pure product at the bottom of the column $F_1$, compared with the overall tert. alkyl ether quantity produced is inadequate. Thus, in the particular case of producing MTAE for an overall conversion of isopentenes of the MTAE charge of approximately 90 to 92%, only approximately 75% of the converted isopentenes are recovered in the pure MTAE.

Under these conditions, it would be of interest to be able to increase the total conversion of the process and/or obtain a higher pure tert. alkyl ether recovery. These are the objectives of the present invention, as defined hereinafter, in conjunction with FIGS. 2, 3 and 4.

In general terms, the process for the preparation of tertiary alkyl ether according to the invention can be defined in that it comprises a first reaction section where contacting takes place between a $C_4$, $C_5$, $C_6$ or $C_7$ hydrocarbon charge containing at least one reactive isoolefin with an aliphatic monoalcohol excess, e.g., containing 1 to 3 carbon atoms, and a fractionation section in which the effluent of the first reaction section is introduced into a fractionation column $F_1$, at the bottom is collected the pure tert. alkyl ether and at the head an effluent which, after condensation, is subdivided into a reflux returned to the head of the fractionation column and a distillate incorporating non-reactive hydrocarbons, hydrocarbons not converted in the first reaction section and the aliphatic monoalcohol excess, said process being characterized in that it comprises a complementary reaction section incorporating at least one finishing reactor on the reflux returned to the head of the fractionation column.

The charge used for preparing the tertiary alkyl ether according to the process of the invention generally contains at least one isoolefin able to react with the aliphatic monoalcohol in the etherification reaction giving rise to the tert. alkyl ether. In the case of the $C_5$ fraction, the reactive isoolefins are more particularly 2-methyl-1-butene and 2-methyl-2-butene. However, 3-methyl-1-butene (another isopentene) is not reactive. The charges can also incorporate other non-reactive unsaturated hydrocarbons and saturated hydrocarbons with the same carbon condensation as the reactive isoolefins.

Usually the treated charges are fractions coming from catalytic cracking and vapor cracking following fractionation. As a function of the fractionation, these charges could also contain small amounts of hydrocarbons having a number of carbon atoms above or below that of the isoolefins to be treated.

Following reaction in the reaction section $R_1$ under conventional conditions (liquid or mixed phase, pressure of 2 to 20 bars, preferably 5 to 15 bars, temperature of 4° to 150° C. and preferably 5° to 100° C.), the effluent leaving the reactor $R_1$ generally contains tert. alkyl ether, non-reactive hydrocarbons contained in the charge, non-converted hydrocarbons and the aliphatic monoalcohol excess. This effluent is fed into the fractionation section, where it is generally distilled under an absolute pressure of 1 to 10 bars and a base temperature of 120° to 140° C.

In all the considered embodiments of the invention, the head effluent passing out of the fractionation section $F_1$ by the line 1 contains the non-reactive hydrocarbons of the charge, the non-converted hydrocarbons and the aliphatic monoalcohol excess. This effluent is condensed in the condenser $E_1$, the condensate, recovered by the line 2 in the flask $B_1$, being taken up by the pump $P_1$.

Figure 2:
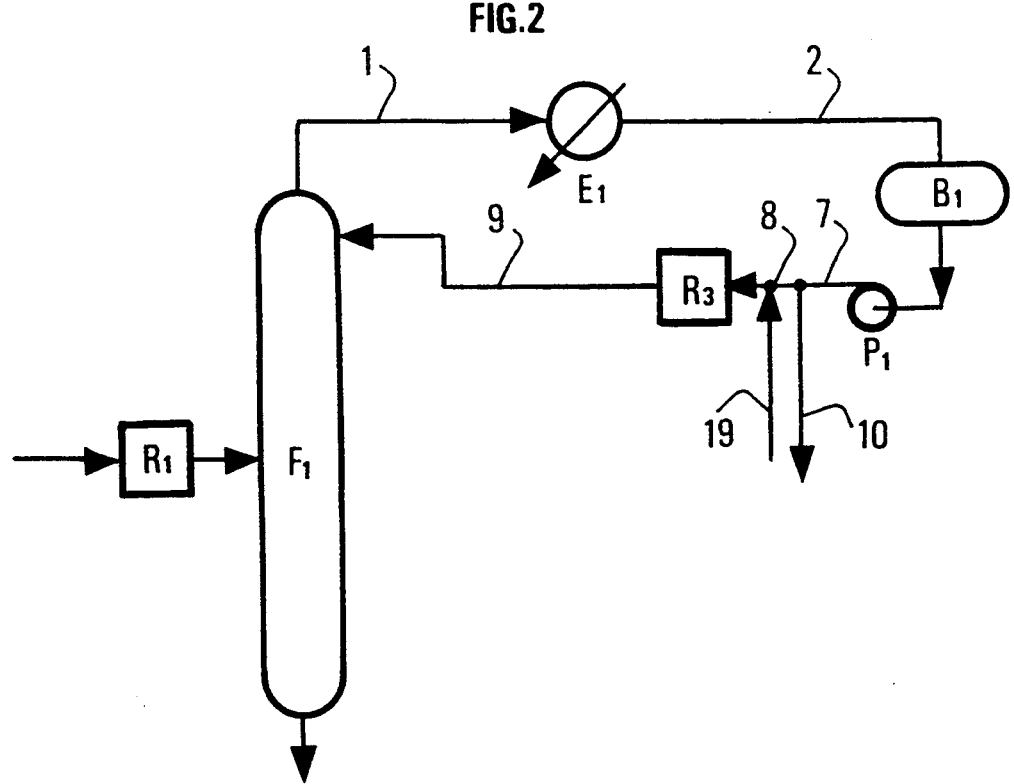
FIG. 2 diagrammatically shows an embodiment of the tert. alkyl ether preparation process according to the invention having a finishing reactor on the reflux.

In the first embodiment of the process according to the invention illustrated in FIG. 2, the product passing out of the pump $P_1$ by the line 7 is subdivided into two flows, namely the reflux and the distillate of the fractionation column $F_1$. The reflux is fed by the line 8 to a finishing reactor $R_3$, in which the unconverted isoolefins and the aliphatic monoalcohol react on an acid catalyst to produce the tert. alkyl ether.

As in the reactor $R_1$, the acid catalyst used can be chosen from among e.g., sulphuric acid, hydrofluoric acid, aluminum chloride, boron fluoride, carbonated/sulphonated materials, such as sulphonated charcoals, sulphonated phenol-formaldehyde resins, sulphonated coumarone-indene polymers or, preferably, sulphonated styrene-divinyl benzene copolymer resins. It is also possible to use a zeolitic catalyst.

The reaction generally takes place on a fixed bed catalyst in the liquid or mixed phase, at a temperature of 40° to 150° C., and preferably 50° to 100° C., and under a pressure of 2 to 20 bars, preferably 5 to 15 bars. The reaction product is recovered by the line 9 and can be supplied as reflux to the head of the fractionation column $F_1$, the thus produced supplementary tert. alkyl ether being recovered at the base of said column, together with the tert. alkyl ether produced in the main reaction section.

In the particular case of the production of MTAE, the total isopentene conversion obtained in this embodiment is approximately 85 to 90%, a proportion of approximately 83 to 85% of the converted isopentenes being recovered in the pure MTAE.

The distillate passing out by the line 10 contains non-reactive hydrocarbons, unconverted hydrocarbons, unconverted aliphatic monoalcohol and small amounts of tert. alkyl ether. It is generally directly supplied to a section for the washing and recovery of the aliphatic monoalcohol (not shown in FIG. 2), from which passes a refined product containing a small amount of tert. alkyl ether, e.g., corresponding to 1 to 5% by weight of the converted isopentenes. In the particular case of MTAE production, this refined product can be used in the petroleum fraction.

Figure 3:
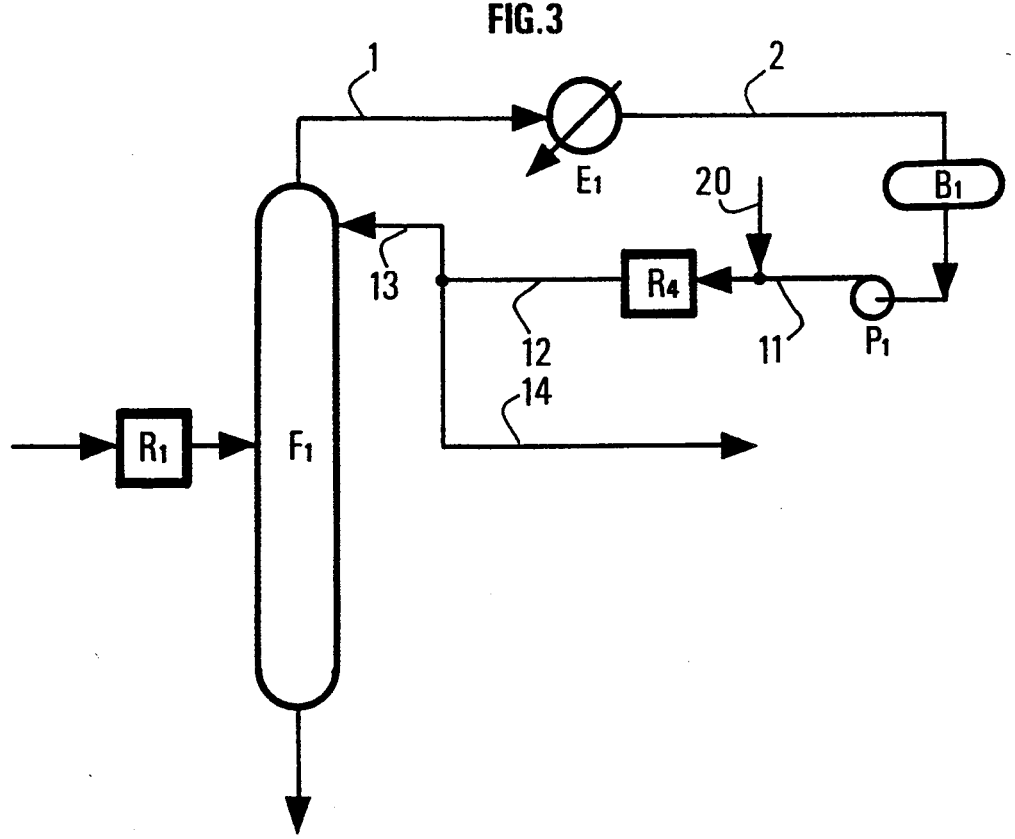
FIG. 3 diagrammatically shows a second embodiment of the process according to the invention, in which the finishing reactor is both on the reflux and on the distillate prior to their separation.

In a second embodiment of the process according to the invention illustrated in FIG. 3, the product passing out of the pump $P_1$ is supplied by the line 11 to a finishing reactor $R_4$, where working takes place under the conditions described in the first embodiment. The effluent passing out of the reactor $R_4$ by the line 12 is subdivided into two flows, the reflux being passed to the head of the fractionation column $F_1$ by the line 13 and the distillate is recovered by the line 14.

In the particular case of MTAE production, the total conversion of isopentenes obtained is approximately 94 to 96%, approximately 82 to 85% of the converted isopentenes being recovered in the pure MTAE.

The distillate recovered by the line 14 contains non-reactive hydrocarbons, unconverted hydrocarbons, unreacted aliphatic monoalcohol and tert. alkyl ether quantities which, in this case, are higher than those obtained in the previous embodiment. This distillate is generally supplied directly to the section for washing and recovering the aliphatic monoalcohol, from which passes a refined product containing, in the particular case of MTAE production, a MTAE proportion corresponding to 10 to 15% by weight of the converted isopentenes. As previously, this refined product is usable in the petroleum fraction.

Figure 4:
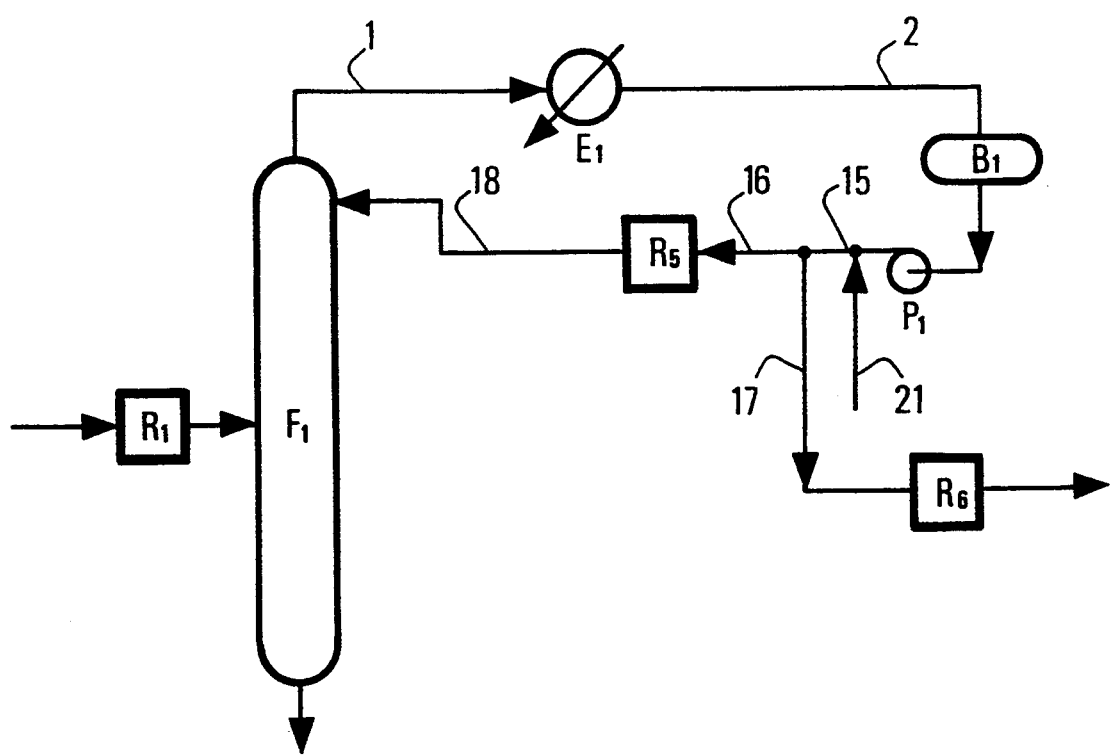
FIG. 4 diagrammatically shows a variant of the second embodiment, in which a finishing reactor is placed on each of the two flows, namely the distillate and the reflux following their separation.

In a variant of this second embodiment of the process according to the invention illustrated in FIG. 4, the product leaving the pump $P_1$ by the line 15 is subdivided into two flows, namely the column distillate and the reflux. The reflux is supplied by the line 16 to a first finishing reactor $R_5$, the distillate being supplied by the line 17 to a second finishing reactor $R_6$, each of the two reactors functioning under the same conditions as described hereinbefore for the reactor $R_3$. The effluent from the reactor $R_5$ is supplied as reflux to the head of the fractionation column $F_1$ by the line 18.

In the particular case of MTAE production, the total conversion of isopentenes into MTAE obtained in this variant, as well as the pure MTAE recovery rate at the base of the fractionation column $F_1$ are of the same order of magnitude as those given for the second embodiment described hereinbefore.

For the two embodiments of the process according to the invention and the variant to the second embodiment as described hereinbefore, it is possible to envisage the injection upstream of each finishing reactor ($R_3$, $R_4$ and $R_5+R_6$ by the lines 19, 20 and 21 respectively) of a complementary quantity of at least one aliphatic monoalcohol, which can be the same alcohol as used in the main etherification reactor, or a different monoalcohol, e.g., chosen from among methanol, ethanol, propanol and isopropanol. Advantageously, the second alcohol will be heavier than that used in the main etherification reactor $R_1$. In this case, both at the base of the column $F_1$ and in the refined product a mixture of tert. alkyl ethers will be obtained, e.g., a mixture of MTAE and ETAE (ethyl tert. amyl ether), in which the MTAE will preponderate. It can also be envisaged to heat the charge of said finishing reactors ($R_3$, $R_4$, $R_5$ and $R_6$), as well as cool the effluents of the finishing reactors installed on the reflux ($R_3$, $R_4$ and $R_5$).

The following examples illustrate the invention, example 1 being given for comparison purposes.

EXAMPLES 1 to 4

MTAE is prepared on the one hand according to the conventional diagram (diagram 1, in conjunction with FIG. 1) and on the other hand according to the embodiments of the invention (diagrams 2, 3 and 4 in conjunction with FIGS. 2, 3 and 4 respectively).

The following table gives the composition of the charge and the conversion of isopentenes in the main reaction section $R_1$ and the operating conditions used in the finishing reactor or reactors $R_3$, $R_4$, $R_5$ and $R_6$ and, for each diagram, the conversions obtained in the finishing reactor, as well as the total conversion, the pure MTAE quantity recovered at the base of the fractionation column $F_1$ and the MTAE concentration in the refined product.

TABLE

|  | Diagram 1 | Diagram 2 | Diagram 3 | Diagram 4 |
|---|---|---|---|---|
| Composition of the charge reactive isopentenes (% by weight) | 23 | 23 | 23 | 23 |
| Isopentene conversion, outlet $R_1$ (% by weight) | 75 | 75 | 75 | 75 |
| Operating conditions in the finishing reactor or reactors | | | | |
| Catalyst: | acid resin (sulphonated styrene-DB copolymer) | | | |
| Reactor type: | fixed bed | | | |
| Phase: | liquid | | | |
| Pressure: | 10 bars | | | |
| Temperature: | 65 to 75° C. | | | |
| Finishing reactor conversion (% by weight) | 68 | 50 | 84 | 50/68 ($R_5$)($R_6$) |
| Total conversion (% by weight) | 92 | 87.5 | 96 | 96 |
| Pure MTAE recovered (expressed as isopentene conversion - % by weight) | 75 | 84 | 84 | 84 |
| Pure MTAE recovered (in kg per 100 kg of charge) | 25.1 | 28.1 | 28.1 | 28.1 |
| MTAE in $C_5$ refined product (expressed as isopentene conversion - % by weight) | 17 | 3.5 | 12 | 12 |
| MTAE in $C_5$ refined product (in kg per 100 kg of charge) | 5.7 | 1.2 | 4 | 4 |

It can be seen that the performance of the process according to diagrams 2, 3 and 4 makes it possible to significantly increase the MTAE proportion recovered in pure form at the base of the column $F_1$. Moreover, the performance of the process according to diagrams 3 and 4 also significantly increases the total isopentene conversion.

We claim:

1. A process for production of at least one tertiary alkyl ether, said process comprising:
   contacting, in a first reactor, a hydrocarbon charge containing at least one reactive isoolefin with excess of an aliphatic monoalcohol, whereby said at least one reactive isoolefin reacts with said aliphatic monoalcohol;
   removing effluent from said first reactor and introducing said effluent into a fractionation column;
   recovering tertiary alkyl ether from the bottom of said fractionation column and removing head effluent from said fractionation column;
   condensing said head effluent in a condenser; and
   subdividing the condensed head effluent into a reflux stream which is fed to the head of said fractionation column and a distillate stream containing non-reactive hydrocarbons, hydrocarbons not converted in said first reaction section and excess aliphatic monoalcohol,
   wherein after condensation of said head effluent, said reflux stream, either upstream or downstream of the subdivision of said head effluent, is introduced into a finishing reactor before said reflux stream is delivered to the head of said fractionation column, said finishing reactor operating at a pressure of 2–20 bar.

2. A process according to claim 1, wherein only said reflux stream is introduced into said finishing reactor.

3. A process according to claim 1, wherein, prior to its subdivision, said head effluent is introduced into said finishing reactor, whereby both said reflux stream and said distillate stream are treated in said finishing reactor.

4. A process according to claim 1, wherein said reflux stream, following subdivision of said head effluent, is introduced into said finishing reactor and said distillate stream is separately treated in another finishing reactor.

5. A process according to claim 1, wherein said charge is a $C_4$, $C_5$, $C_6$ or $C_7$ fraction.

6. A process according to claim 1, wherein said aliphatic monoalcohol is methanol, ethanol, propanol or isopropanol.

7. A process according to claim 1, wherein said charge is a $C_5$ fraction, said aliphatic monoalcohol is methanol, and said at least one tert. alkyl ether is methyl tert. amyl ether.

8. A process according to claim 1, wherein said finishing reactor is a fixed bed reactor and the reaction conducted in said finishing reactor is performed in the liquid phase or in a mixed phase at a temperature of 40° to 150° C. and under a pressure of 2 to 20 bars.

9. A process according to claim 1, wherein said finishing reactor contains an acid catalyst selected from the group consisting of sulphuric acid, hydrofluoric acid, aluminum chloride, boron fluoride, sulphonated/carbonated materials, sulphonated phenol-formaldehyde resins, sulphonated coumarone-indene polymers, sulphonated styrene-divinyl benzene copolymer resins and zeolitic catalysts.

10. A process according to claim 9, wherein said acid catalyst is a sulphonated styrene-divinyl benzene copolymer resin.

11. A process according to claim 1, wherein at least one aliphatic monoalcohol selected from the group consisting of methanol, ethanol, propanol and isopropanol is injected upstream of said finishing reactor.

12. A process according to claim 1, further comprising preheating said reflux stream before introduction thereof into said finishing reactor.

13. A process according to claim 1, wherein, after discharge from said finishing reactor, said reflux stream is cooled before introduction into the head of said fractionation column.

14. A process for the production of at least one tertiary alkyl ether, said process comprising:
   reacting a hydrocarbon charge containing at least one reactive isoolefin with an excess of an aliphatic monoalcohol in a first catalytic reactor, said first catalytic reactor contains an acid catalyst and operates at a pressure of 2–20 bar and a temperature of 4°–150° C., the reaction between said at least one reactive isoolefin and said aliphatic monoalcohol is performed in the liquid or mixed phase, wherein said at least one reactive isoolefin is a $C_4$, $C_5$, $C_6$ or $C_7$ isoolefin and said aliphatic monoalcohol is methanol, ethanol, propanol or isopropanol;

removing effluent from said first reactor and introducing said effluent into a fractionation column operating at a pressure of 1–10 bar and a temperature of 120°–140° C., said fractionation column having a head section and a bottom section;

recovering tertiary alkyl ether from said bottom section of said fractionation column and removing head effluent from said head section of said fractionation column;

condensing said head effluent in a condenser and subdividing the condensed head effluent into a reflux stream and a distillate stream;

after, subdivision of said condensed head effluent, introducing said reflux stream into a catalytic finishing reactor containing an acid catalyst, wherein unconverted isoolefins and aliphatic monoalcohol are reacted, said finishing reactor operating at a temperature of 40°–150° C. and a pressure of 2–20 bar, the reaction in said finishing reactor being performed in the liquid phase or mixed phase; and removing said reflux stream from said finishing reactor and delivering said reflux stream to said head section of said fractionation column.

15. A process according to claim 14, wherein at least one aliphatic monoalcohol selected from the group consisting of methanol, ethanol, propanol and isopropanol is injected into said reflux stream after subdivision of said condensed head effluent and prior to introduction of said reflux stream into said finishing reactor.

16. A process for the production of at least one tertiary alkyl ether, said process comprising:

reacting a hydrocarbon charge containing at least one reactive isoolefin with an excess of an aliphatic monoalcohol in a first catalytic reactor, said first catalytic reactor contains an acid catalyst and operates at a pressure of 2–20 bar and a temperature of 4°–150° C., the reaction between said at least one reactive isoolefin and said aliphatic monoalcohol is performed in the liquid or mixed phase, wherein said at least one reactive isoolefin is a $C_4$, $C_5$, $C_6$ or $C_7$ isoolefin and said aliphatic monoalcohol is methanol, ethanol, propanol or isopropanol;

removing effluent from said first reactor and introducing said effluent into a fractionation column operating at a pressure of 1–10 bar and a temperature of 120°–140° C., said fractionation column having a head section and a bottom section;

recovering tertiary alkyl ether from said bottom section of said fractionation column and removing head effluent from said head section of said fractionation column;

condensing said head effluent in a condenser and subdividing the condensed head effluent into a reflux stream and a distillate stream;

after, subdivision of said condensed head effluent, introducing said reflux stream into a catalytic finishing reactor containing an acid catalyst, wherein unconverted isoolefins and aliphatic monoalcohol are reacted, said finishing reactor operating at a temperature of 40°–150° C. and a pressure of 2–20 bar, the reaction in said finishing reactor being performed in the liquid phase or mixed phase;

removing said reflux stream from said finishing reactor and delivering said reflux stream to said head section of said fractionation column; and introducing said distillate stream into a second finishing reactor and delivering said distillate stream to said head section of said fractionation column.

17. A process according to claim 16, wherein, after condensation of said head effluent and prior to subdivision of the condensed head effluent, at least one aliphatic monoalcohol selected from the group consisting of methanol, ethanol, propanol and isopropanol is injected into said condensed head effluent.

18. A process according to claim 11, wherein said at least one aliphatic monoalcohol injected upstream of said finishing reactor is heavier than said at least one aliphatic monoalcohol introduced into said first reactor.

19. A process for the production of at least one tertiary alkyl ether, said process comprising:

reacting a hydrocarbon charge containing at least one reactive isoolefin with an excess of an aliphatic monoalcohol in a first catalytic reactor, said first catalytic reactor contains an acid catalyst and operates at a pressure of 2–20 bar and a temperature of 4°–150° C., the reaction between said at least one reactive isoolefin and said aliphatic monoalcohol is performed in the liquid or mixed phase, wherein said at least one reactive isoolefin is a $C_4$, $C_5$, $C_6$ or $C_7$ isoolefin and said aliphatic monoalcohol is methanol, ethanol, propanol or isopropanol;

removing effluent from said first reactor and introducing said effluent into a fractionation column operating at a pressure of 1–10 bar and a temperature of 120°–140° C., said fractionation column having a head section and a bottom section;

recovering tertiary alkyl ether from said bottom section of said fractionation column and removing head effluent from said head section of said fractionation column;

condensing said head effluent in a condenser and subdividing the condensed head effluent into a reflux stream and a distillate stream;

prior to subdivision of said condensed head effluent, introducing said head effluent into a catalytic finishing reactor containing an acid catalyst, wherein unconverted isoolefins and aliphatic monoalcohol are reacted, said finishing reactor operating at a temperature of 40°–150° C. and a pressure of 2–20 bar, the action of said finishing reaction being performed in a liquid phase or a mixed phase;

prior to introduction of said condensed head effluent into said catalytic finishing reactor, at least one aliphatic monoalcohol selected from the group consisting of methanol, ethanol, propanol and isopropanol is injected into said head effluent; and delivering said reflux stream to said head section of said fractionation column.

20. A process according to claim 19, wherein said at least one aliphatic monoalcohol injected into said head effluent is heavier than said aliphatic monoalcohol introduced into said first reactor.

* * * * *